United States Patent [19]

Furda

[11] Patent Number: 5,736,532
[45] Date of Patent: Apr. 7, 1998

[54] MULTIFUNCTIONAL FAT ABSORPTION AND BLOOD CHOLESTEROL REDUCING FORMULATION COMPRISING CHITOSAN

[76] Inventor: Ivan Furda, 16664 Meadowbrook La., Wayzata, Minn. 55391

[21] Appl. No.: 601,388

[22] Filed: Feb. 14, 1996

[51] Int. Cl.$^6$ .................................................. A61K 31/73
[52] U.S. Cl. ................................................................ 514/55
[58] Field of Search ................................................... 514/55

[56] References Cited

U.S. PATENT DOCUMENTS

| | | | |
|---|---|---|---|
| 4,223,023 | 9/1980 | Furda | 514/55 |
| 5,453,282 | 9/1995 | Kanauchi et al. | 424/464 |

OTHER PUBLICATIONS

M. Sugano et al., American Journal of Clinical Nutrition, 33, Apr. 1980, pp. 787–793.

Y. Maezaki et al., Biosci. Biotech. Biochem., 1993, 57 (9), pp. 1439–1444.

K. Deuchi et al., Biosci. Biotech. Biochem., 1994, 58 (9), pp. 1613–1616.

I. Furda, "Unconventional Sources of Dietary Fiber," ACS Symposium Series, vol. 214, 1983, pp. 105–122.

M.L. Wahlqvist, "Effects on Plasma Cholesterol of Nicotinic Acid and its Analogues," Vitamins in Human Biology and Medicine, Chapter 4, edited by H. Briggs, CRC Press, 1981, pp. 81–94.

C.D. Moutafis et al., Atherosclerosis, 1971, 14, pp. 247–258.

O. Kanauchi et al., Biosci. Biotech. Biochem., 1995, 59 (5), pp. 786–790.

Vahouny et al. *The American Journal of Clinical Nutrition* Aug. 1983, 38, 278–284.

*Primary Examiner*—Kathleen K. Fonda
*Attorney, Agent, or Firm*—Sprung Kramer Schaefer & Briscoe

[57] ABSTRACT

Chitosan is formulated with nicotinic acid and may additionally contain one or more other vitamin acids, such as ascorbic acid, folic acid, pantothenic acid, or biotin, for oral administration to enhance cholesterol reduction and high-density lipoprotein elevation in blood serum. In addition, such formulations reduce the pH of large intestine which is beneficial in colon etiology. The formulation may be in dosage unit form for daily administration of, for example, 2–18 g of chitosan and 50–3,000 mg of nicotinic acid.

11 Claims, No Drawings

MULTIFUNCTIONAL FAT ABSORPTION AND BLOOD CHOLESTEROL REDUCING FORMULATION COMPRISING CHITOSAN

BACKGROUND OF THE INVENTION

In my U.S. Pat. No. 4,223,023 of Sep. 16, 1980, the use of chitosan to reduce lipid absorption by oral administration is described. The chitosan may be used as such, i.e., as the free base, or in the form of a fatty acid complex.

Chitosan (1-4-β-D-polyglucosamine), usually containing about 0–30% of N-acetylglucosamine residues, has been confirmed in numerous animal and clinical studies as being an effective cholesterol-reducing agent. It, additionally, has been shown to act as a powerful fat binder, binding dietary fats in vivo and thus rendering them nutritionally unavailable. The bound fats, instead of being absorbed and utilized, are excreted. While the mechanism of chitosan's activity in mammals is complex, and several different modes of action have been proposed, it is believed that chitosan acts in a non-systemic manner, and the critical process takes place in the digestive tract of the mammal.

SUMMARY OF THE INVENTION

An object of this invention is a chitosan formulation that has improved hypolipidemic efficiency, is more effective in elevating high-density lipoprotein fraction (HDL) in blood serum, reduces the pH of large intestine, and has a better nutritional profile. These and further objects will become apparent from the following description.

DETAILED DESCRIPTION OF THE INVENTION

In accordance with the invention, chitosan is formulated with nicotinic acid in a form which may be orally administered to mammals, such as humans. The formulation should be in a form to allow administration of about 2–18 grams per day of chitosan with 50–3,000 milligrams per day of nicotinic acid. The formulation is preferably in the form of a powder mixture and should contain a weight ratio of chitosan to nicotinic acid between about 0.67 and 360. The powder may, for example, be incorporated into individual gelatin capsules in dosage unit form, or may be formed into tablets, or the like, by conventional procedures.

The chitosan and nicotinic acid may be formulated by dry mixing the components in powder form, or, for example, by treating chitosan free base with an aqueous solution of nicotinic acid (niacin) to form chitosan-nicotinate salt, followed by drying.

The formulation, preferably, additionally contains one or more other water-soluble vitamin acids, such as ascorbic acid, folic acid, pantothenic acid, or biotin. These additional acids should preferably be present in amounts to provide a daily dosage of, for example, 50–3,000 mg/day ascorbic acid, 200–400 mcg/day folic acid, 5–10 mg/day pantothenic acid, and 150–300 mcg/day biotin. These acids may be added as a dry mix or by neutralization of the chitosan as a free base with an aqueous solution of one or more of such vitamin acids to prepare corresponding salts, followed by drying.

The combination of the chitosan with the nicotinic acid and/or with the other water-soluble vitamin acids has an additional and unique effect in that the chitosan delays vitamin rapid absorption. This is achieved by ionic binding of vitamin acids to unabsorbable chitosan as well as by increased viscosity caused by the administered or in situ formed chitosan-vitamin acid salts. The presence of water soluble vitamin acids in the lower digestive tract results in lowering of its pH which is beneficial in reducing the risk of large bowel cancer development.

The chitosan, as used herein, in addition to being in the form of the free base in which it normally exists, can be in the form of the hydrochloride or other chitosan salts, after being partially neutralized by hydrochloric or other acids.

Unexpectedly, the components of the formulation in accordance with the invention, synergistically act when orally administered to mammals, such as humans, to enhance reduction of serum lipids, namely total cholesterol and LDL, while increasing HDL, thus providing benefits for individuals who desire to reduce the risks associated with coronary heart disease, high blood pressure and obesity.

The formulation in accordance with the invention additionally provides a better nutritional profile.

The formulation furthermore minimizes the recognized adverse side effects caused by nicotinic acid when used in high doses.

The formulation, because of the presence of vitamin acids, insures a more complete solubilization of the chitosan under gastric conditions. The increased solubilization increases the chitosan surface area and its initial intestinal viscosity as it enters the upper gastrointestinal tract, namely the duodenum and jejunum. It is known that greater intestinal viscosity enhances the hypocholesterolemic effect of unabsorbable fibers, which is reflected in blood serum. It is also known, however, that very high concentration of ascorbic acid or its sodium salt enhances chitosan's fat binding, as reflected by increased fat excretion. This effect, in contrast to the enhanced blood cholesterol reduction, is believed to be due to reduced gastric viscosity or to other factors caused by the very high level of these compounds in the diet of experimental animals (1.5%).

The formulation may additionally contain other water-soluble vitamins and oil-soluble vitamins, such as Vitamin A, E, D and K, as well as B-Carotene, for their nutritional value, though the same have not been shown to improve the hypolipidemic efficiency.

The formulation of the chitosan with the water-soluble vitamin acids furthermore comprises an unique system for the delivery of these biologically active vitamin acids. Chitosan has been found to bind these vitamin acids, providing a viscous environment, thus slowing down their absorption, in effect, acting as a slow-release agent. Additionally, as their absorption is slowed down, they can partially reach the large intestine, having a desirable effect on colonic pH. The chitosan can enhance delayed absorption of both basic water-soluble vitamins, such as thiamine, riboflavin, pyridoxine and Vitamin $B_{12}$, and oil-soluble vitamins.

The following examples are given by way of illustration and not limitation.

EXAMPLE 1

| Preparation of Chitosan - Nicotinic Acid Dry Mix for Oral Administration | |
|---|---|
| Ingredients | Grams |
| Chitosan powder | 983.3 |
| Nicotinic acid powder | 16.7 |

An intimate mixture of these ingredients is prepared in a mixer or blender and is then packed into individual gelatin capsules containing 250 milligrams of powder. The dosage is five to eight capsules, ingested during or after a meal, preferably with a generous amount of liquid (approximately 8 fluid ounces) three times daily. The maximum total daily intake of chitosan in that case (24 capsules) is 5.9 grams, and that of nicotinic acid is 100 mg, which represents 500% RDA for nicotinic acid.

EXAMPLE 2

Preparation of Chitosan-Nicotinate by Partial Neutralization of Chitosan with Nicotinic Acid Fine powder of chitosan free base (90.00 g) is dispersed in 1000 ml of aqueous solution of nicotinic acid (10.00 g). The dispersion is stirred vigorously for two hours at room temperature. The dispersion is then filtered or centrifuged, and the product is washed with water and alcohol, and dried. The dried powder is then formed into tablets with tableting aids, or packed into individual gelatin capsules containing 250 mg of powder. The dosage is five to eight capsules, ingested during or after a meal, preferably with a generous amount of liquid (approximately 8 fluid ounces) three times daily.

EXAMPLE 3

| Preparation of Chitosan-Vitamin Acids Dry Mix for Oral Administration | |
|---|---|
| Ingredients | Grams |
| Chitosan powder | 814.45 |
| Nicotinic acid | 167.00 |
| Pantothenic acid | 1.68 |
| Ascorbic acid | 16.80 |
| Folic acid | 67 mg |
| Biotin | 50 mg |

An intimate mixture of these ingredients is prepared in a mixer or blender and is then packed into individual gelatin capsules containing 250 milligrams of powder. The dosage is five to eight capsules, ingested during or after a meal, preferably with a generous amount of liquid (approximately 8 fluid ounces) three times daily. The maximum daily intake of 24 capsules would correspond, in that case, to

| Acid | mg | % RDA |
|---|---|---|
| Nicotinic | 1,000 | 5,000 |
| Pantothenic | 10 | 100 |
| Ascorbic | 100 | 167 |
| Folic | 0.4 | 100 |
| Biotin | 0.3 | 100 |

Although the invention has been described in detail with reference to certain specific embodiments, various changes and modifications will become apparent to those skilled in the art. The invention is only intended to be limited by the appended claims or their equivalents.

What is claimed is:

1. A cholesterol reduction formulation comprising chitosan and nicotinic acid, said chitosan being present in a weight amount relative to the nicotinic acid of between 0.67 and 360.

2. Formulation according to claim 1, in which said formulation is in the form of a dry powder mixture of chitosan and nicotinic acid.

3. Formulation according to claim 1, in which said chitosan and nicotinic acid are present in said formulation at least partially in the form of chitosan-nicotinate salt and prepared by treating chitosan free base with an aqueous solution of niacin.

4. Formulation according to claim 1 in dosage unit form.

5. Formulation according to claim 4, in which said dosage unit formulation is in the form of gelatin capsules containing a powder mixture of the formulation.

6. Formulation according to claim 1, containing at least one additional water-soluble vitamin acid.

7. Formulation according to claim 6, in which said water-soluble vitamin acid is selected from the group consisting of ascorbic acid, folic acid, pantothenic acid, and biotin.

8. In a method of reducing cholesterol in mammals by the oral administering of chitosan to bind and excrete the cholesterol, the improvement which comprises administering the chitosan in a combination with nicotinic acid at a relative weight ratio of chitosan to nicotinic acid of between 0.67 and 360 to thereby increase the amount of cholesterol bound by the chitosan.

9. Method according to claim 8, in which the chitosan and nicotinic acid are at least partially present in the form of a chitosan-nicotinate salt.

10. Method according to claim 8, in which a vitamin selected from the group consisting of ascorbic acid, folic acid, pantothenic acid, and biotin is additionally administered with the combination.

11. Method according to claim 8, in which 2–18 grams per day of chitosan and 50–3,000 milligrams per day of nicotinic acid are administered.

* * * * *